(12) United States Patent
Wu et al.

(10) Patent No.: US 7,566,690 B2
(45) Date of Patent: Jul. 28, 2009

(54) ACE INHIBITORY PEPTIDES FROM PLANT MATERIALS

(75) Inventors: Jian-ping Wu, Saskatoon (CA); Alister D. Muir, Saskatoon (CA); Rotimi E. Aluko, Winnipeg (CA)

(73) Assignee: Her Majesty the Queen in right of Canada as represented by the Minister of Agriculture and Agri-food Canada, Saskatchewan (CA)

( * ) Notice: Subject to any disclaimer, the term of this patent is extended or adjusted under 35 U.S.C. 154(b) by 0 days.

(21) Appl. No.: 10/538,951

(22) PCT Filed: Dec. 24, 2003

(86) PCT No.: PCT/CA03/02020

§ 371 (c)(1),
(2), (4) Date: Mar. 28, 2006

(87) PCT Pub. No.: WO2004/057976

PCT Pub. Date: Jul. 15, 2004

(65) Prior Publication Data

US 2006/0217318 A1     Sep. 28, 2006

Related U.S. Application Data

(60) Provisional application No. 60/435,866, filed on Dec. 24, 2002.

(51) Int. Cl.
| | | |
|---|---|---|
| A61K 38/00 | (2006.01) | |
| A01N 37/18 | (2006.01) | |
| A61K 51/00 | (2006.01) | |
| A61M 36/14 | (2006.01) | |

(52) U.S. Cl. .......................................... 514/2; 424/1.69
(58) Field of Classification Search ....................... None
See application file for complete search history.

(56) References Cited

U.S. PATENT DOCUMENTS

| 4,175,075 | A | * | 11/1979 | Garrison et al. ............. 530/377 |
| 4,739,076 | A | | 4/1988 | Southwick |
| 5,705,618 | A | | 1/1998 | Westcott et al. |
| 6,232,438 | B1 | | 5/2001 | Shin et al. |

FOREIGN PATENT DOCUMENTS

| EP | 1094071 A1 | 4/2001 |
| JP | 04349893 | 12/1992 |
| JP | 06 016568 | 1/1994 |
| WO | 406016568 A * | 1/1994 |
| WO | WO 99/65326 A1 | 12/1999 |

OTHER PUBLICATIONS

Wu J et al. "Hypotensive and Physiological Effect of Angiotensin Converting Enzyme Inhibitory Peptides Derived From Soy Protein on Spontaneously Hypertensive Rats" 2001, J. Agric. Food Chem. vol. 49, pp. 501-506.*

Wu et al. "Hypotensive and Physiological Effect of Angiotensin Converting Enzyme'Inhibitory Peptides Derived from Soy Protein on Spontaneously Hypertensive Rats" 2001, J. Agric. Food Chem. vol. 49. pp. 501-506.*
Eto et al. "Angiotensin I Converting Enzyme-Inhibitory Dipeptides in an Alkaline Protease Hydrolysate of Whey Protein" 1998, J. Jpn. Soc. Nutr. Food Sci. vol. 51. pp. 355-359.*
Tzen et al. "Lipids, Proteins and Structure of Seed Oil Bodies from Diverse Species" 1993, Plant Physiol. vol. 101. pp. 267-276.*
Adler-Nissen, J.(1979), "Determination of the Degree of Hydrolysis of Food Protein Hydrolysates by Trinitrobenzenesulfonic Acid", J. Agric. Food Chem., v. 27, pp. 1256-1262.
Adler-Nissen, J. (1986), "Methods in Food Protein Hydrolysis", Elsevier Applied Science Publishing, pp. 110-131.
Baek et al.,(1995), J. Food Sci., v. 60, pp. 929-935.
Cushman et al.,(1971), "Spectrophotometric Assay and Properties of the Angiotensin-Converting Enzyme of Rabbit Lung", Biochem. Pharmacol., v. 20, pp. 1637-1648.
Eto et al.,(1998), "Angiotensin I Converting Enzyme-inhibitory Dipeptides in an Alkaline Protease Hydrolysate of Whey Protein", J. Jpn. Soc. Nutr. Food Sci., v. 51, pp. 355-359, Abstract-XP-008003054.
Ferreira, S.H.(1965) "A Bradykinin-Potentiating Factor (BPF) Present in the Venom of Bothrops Jararaca", British Journal of Pharmacology, v. 24, pp. 63-169.
Flynn et al.,(1993), "Application of a Conformationally Restricted Phe-Leu Dipeptide Mimetic to the Design of a Combined Inhibitor of Angiotensin I-Converting Enzyme and Neutral Endopeptidase 24.11", J. Med. Chem., v. 36, pp. 2420-2423.
Kawakami et al.,(1995), "Preparations of Enzymatic Hydrolysates of Buckwheat Globulin and Their Angiotensin I Converting Enzyme Inhibitory Activities", Current Advances in Buckwheat Research, pp. 927-934.
Pedroche et al.,(2002), "Utilisation of chickpea protein isolates for production of peptides with angiotensin I-converting enzyme (ACE)-inhibitory activity", J. Sci. Food Agric., v. 82, pp. 960-965.
Skeggs et al.,(1955), "The Preparation and Function of the Hypertensin-Converting Enzyme", J. Exp. Med., v. 103, pp. 295-299.
Wu et al., (2002a), "Characterization of inhibition and stability of soy-protein-derived angiotensin I-converting enzyme inhibitory peptides", Food Res. Intnl., v. 35, pp. 367-375.
Wu et al.,(2002b), "Improved method for direct high-performance liquid chromatography assay of angiotensin-converting enzyme-catalyzed reactions" J. Chrom. A., v. 950(1/2), pp. 125-130.
Yang et al.,(1970), "A dipeptidyl carboxypeptidase that converts angiotensin I and inactivates bradykinin", Biochem. Biophys. Acta, v. 214, pp. 374-376.
Yano et al.,(1996), "Isolation from α-Zein of Thermolysin Peptides with Angiotensin I-Converting Enzyme Inhibitory Activity" Biosci. Biotech. Biochem. V. 60(4), pp. 661-663.

* cited by examiner

*Primary Examiner*—Cecilia Tsang
*Assistant Examiner*—Maury Audet
(74) *Attorney, Agent, or Firm*—Myers Bigel Sibley & Sajovec, P.A.

(57) ABSTRACT

Improved processes are provided for preparing ACE inhibitory peptide containing hydrolysates from a plant material such as a seed meal or flour. In one embodiment, the seed meal or flour is extracted with an organic solvent prior to digestion. Also provided are ACE inhibitory peptides Val-Ser-Val and Phe-Leu.

20 Claims, 3 Drawing Sheets

ACE INHIBITORY PEPTIDES FROM PLANT MATERIALS

RELATED APPLICATION INFORMATION

The present application is a 35 U.S.C. § 371 National Phase Application of International Application Serial No. PCT/CA2003/002020, filed on Dec. 24, 2003, which claims priority from U.S. Provisional Application Ser. No. 60/435,866, filed Dec. 24, 2002, the disclosures of which are incorporated herein by reference in their entireties.

FIELD OF THE INVENTION

This invention relates to improved processes for obtaining ACE inhibitory peptide compositions with high specific activity from plant sources.

BACKGROUND OF THE INVENTION

Hypertension, or high blood pressure, is a common health problem; in North America, one in four adults has hypertension. Since hypertension is asymptomatic, irreversible cardiovascular complications may have arisen before the hypertension is even recognised.

One enzyme which plays a key physiological role in the regulation of blood pressure is angiotensin converting enzyme (ACE: peptidyldipeptide hydrolase, EC 3,4,15,1). ACE is involved in increasing blood pressure both through the renin-angiotensin system, by virtue of its ability to convert the inactive decapeptide angiotensin I to the vasoconstrictive and salt-retaining peptide angiotensin II (Skeggs et al., 1956) and through the kallikrein-kinin system, by virtue of its ability to inactivate the vasodilator and natriuretic nonapeptide, bradykinin (Yang et al., 1970).

Inhibition of ACE activity therefore provides a means of lowering blood pressure.

The first potent and specific inhibitors of ACE activity were discovered by Ferreira (1965), who showed that an extract of the venom of the Brazilian arrowhead viper, *Bothrops jararaca*, potentiated smooth muscle contraction, caused hypotension and increased the capillary permeability induced by bradykinin. The so-called 'bradykinin potentiating factors' (BPF's) were later isolated from a number of snake venoms and found to be short peptides which are potent ACE inhibitors.

A class of synthetic ACE inhibitors has also been made and marketed commercially, the first being captopril (D-2-methyl-3-mercaptopropanoyl-L-proline). Although many drugs of this group have been found to be invaluable for lowering high blood pressure, their prolonged use can be accompanied by unwanted side effects. There therefore remains a need for new therapeutic agents to control hypertension.

It has been known for some time that ACE inhibitory peptides can be obtained by proteolytic digestion of proteins from various sources, including fish (eg. EP 1094071), animal milk proteins (eg. WO 99/65326) and plants (eg. Kawakami et al., (1995); Yano et al., (1996); Pedroche et al., (2002); Wu et al., (2002)). Most of the methods described for obtaining ACE inhibitory peptides from plant proteins involve preliminary purification of the protein before hydrolysis, which adds to the cost and complexity of the process and therefore to the cost of the product.

There remains a need for improved processes for preparing ACE inhibitory compositions from plant materials and for further sources of ACE inhibitory peptides of high specific activity.

SUMMARY OF THE INVENTION

In accordance with one embodiment of the invention is a process for preparing an angiotensin converting enzyme (ACE) inhibitory peptide-containing hydrolysate comprising
contacting a substantially oil-free seed meal or a flour with an organic solvent,
separating the meal or flour from the solvent, and
treating the meal or flour with at least one proteolytic enzyme to produce an ACE inhibitory peptide-containing hydrolysate.

In accordance with a further embodiment is a process for preparing an ACE inhibitory peptide-containing hydrolysate from flax or canola comprising
treating a substantially oil-free flax seed meal or a substantially oil-free canola seed meal with at least one proteolytic enzyme to produce an ACE inhibitory peptide-containing hydrolysate.

In accordance with a further embodiment is an ACE inhibitory peptide-containing hydrolysate prepared by a process as described above.

In accordance with a further embodiment is an ACE inhibitory peptide-containing hydrolysate produced by partial proteolytic digestion of a flax meal or a canola meal.

In accordance with a further embodiment is a powder produced by drying a hydrolysate in accordance with the invention.

In accordance with a further embodiment is an edible food product comprising a hydrolysate in accordance with the invention.

In accordance with a further embodiment is a pharmaceutical composition comprising at least one of peptides Val-Ser-Val and Phe-Leu and a pharmaceutically acceptable carrier.

In accordance with a further embodiment is a peptide of the formula Val-Ser-Val.

In accordance with a further embodiment is a peptide of the formula Phe-Leu.

In accordance with a further embodiment is a method of inhibiting ACE activity in a mammal comprising administering to the mammal an effective amount of a hydrolysate or powder or edible product or composition in accordance with the invention.

Such inhibition of ACE activity can be used to produce a lowering of elevated blood pressure in the mammal. The invention thus provides a method and compositions for treating elevated blood pressure in a mammal, including a human subject.

The invention further provides use of a hydrolysate or powder or edible product or composition in accordance with the invention for preparation of a medicament for the treatment of elevated blood pressure in a mammal, including a human subject.

SUMMARY OF THE DRAWINGS

Certain embodiments of the invention are described, reference being made to the accompanying drawings, wherein.

DETAILED DESCRIPTION OF THE INVENTION

Figure 1:
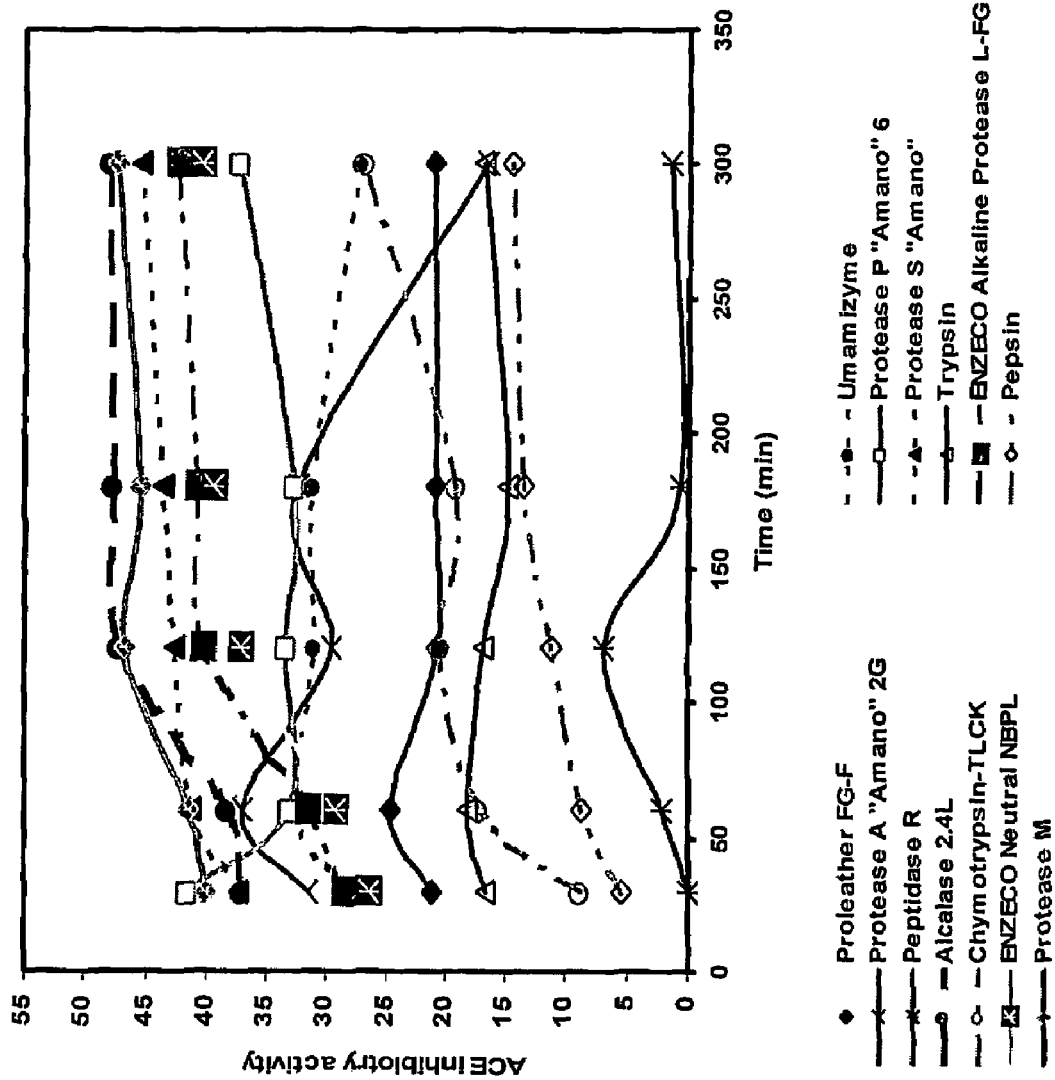
FIG. 1 shows ACE inhibitory activity (Y axis) as a function of incubation time (X axis), for various proteolytic enzymes acting on canola meal.

The present invention provides improved processes and new sources for preparing an ACE inhibitory composition from a plant material such as a meal or a flour without the need to first isolate a highly enriched or purified protein fraction from the plant material.

As used herein, a "meal" means the non-oil portion of oilseeds after oil extraction, in ground form, and a "flour" means the ground seed of a non-oil producing plant such as a cereal or a legume. The processes of the invention may be applied, for example, to oilseed meals produced by conventional methods such as flaking or expelling an oil seed and defatting and solvent extraction of the resulting meal and to flours obtained from non-oil seeds, such as cereals, pseudocereals and legumes.

A "hydrolysate" as used herein means the digestion mixture obtained after proteolytic digestion or partial proteolytic digestion of a seed meal or flour.

In accordance with one embodiment of the invention, the inventors have found that extracting a seed meal or flour with an organic solvent, prior to proteolytic digestion to produce ACE inhibitory peptides, provides hydrolysates with increased ACE inhibitory activity. By using the organic solvent extraction step, the inventors have been able to overcome problems of low yield and low ACE-inhibitory activity which can be encountered when plant material is subjected to direct proteolytic digestion. Table 1 shows that for most plant materials tested, organic solvent extraction of the meal or flour prior to proteolytic digestion increased IC50 and protein content of the hydrolysate.

The plant material to be processed may be obtained from an oil-seed, such as flax, canola/rapeseed, soybean, cottonseed, sunflower, peanut or mustard, from a legume seed, such as soybeans, peas, lentils, beans or chickpeas or from a cereal grain such as wheat, oats, barley or rye or a pseudocereal such as buckwheat.

For oil seeds such as canola, flax and soybean, substantially oil-free seed meal is obtained by subjecting the seed to conventional defatting or oil-extraction methods such as expelling, expelling with solvent extraction and flaking and solvent extraction, as practiced in the commercial vegetable oil industry. The resulting material usually contains less than 1% fat. Seeds such as cereal and pseudocereal grains (eg. wheat, oats, rye, buckwheat) are naturally substantially oil free and do not require defatting.

The ground plant material can be in the form of grits obtained by coarsely grinding the whole seed or defatted meal, followed by screening to give particles classified as coarse (10-20 mesh), medium (20-40 mesh) or fine (40-80 mesh) grits according to size, or the ground plant material may be in the form of flour produced by grinding to very fine particles, so that 97% of the product passes through 100-mesh screen. The hull, husk and bran which are generally low in protein may be removed prior to production of the flour.

Suitable organic solvents for extraction of the meal or flour include the lower alcohols such as methanol, ethanol, propanol and butanol, or acetone or ethyl acetate. Ethanol is preferred. The alcohols may be used alone or as an aqueous mixture containing at least 50% alcohol. 65% to 75% ethanol is preferred.

The organic solvent may be mixed with the seed meal or flour at a liquid:solid ratio in the range of about 8:1 to about 25:1, about 10:1 to about 20:1 being preferred.

The seed meal or flour is kept in contact with the organic solvent for about 1 hour up to about 24 hours, at a temperature from about 20° C. to the boiling point of the organic solvent. In one embodiment, solvent treatment is for 24 hours at room temperature (25° C.), or a shorter time at a higher temperature, eg. 3 hours at 50° C. The meal/solvent slurry may be stirred or otherwise agitated during the contact period.

The treated meal or flour is then separated from the liquid solvent phase by any suitable conventional method, such as centrifugation, screening, filtration or decantation and may be washed with water to reduce the level of residual organic solvent. The material is then ready for proteolytic digestion to generate ACE inhibitory peptides. Alternatively, the residual organic solvent may be removed by hot air drying to produce a meal or flour that can be stored for future rewetting and proteolytic digestion.

Proteolytic digestion of the seed meal or flour to yield ACE inhibitory peptides may be carried out generally by methods known to those of skill in the art, and as further described herein. Suitable proteolytic enzymes include acid, neutral and alkaline proteases, and peptidases, including serine endopeptidases and metallo endopeptidases, or mixtures thereof. Many commercially available proteolytic enzymes can be used, such as those listed in Table 2. One of skill in the art can readily determine the appropriate digestion conditions for the particular proteolytic enzyme employed.

It is also within the skill of one in the art to determine which proteolytic enzyme gives the lowest ACE inhibitory IC50 in the hydrolysate for a particular plant material, as described in the examples and in FIG. 1. It has been found, for example, that thermolysin gives the best inhibitory activity of the enzymes tested when used for digestion of flax seed meal and soybean meal. Proteolysis may be carried out for a period of time which yields the lowest ACE inhibitory IC50 in the hydrolysate. Generally, a digestion period of about 3 hours provides maximum inhibitory activity.

If the hydrolysate is to be used as an edible product such as a food or a food supplement, it may be desirable to stop the proteolytic digestion before maximum ACE inhibitory activity is achieved, in order to retain some of the food value of the plant protein. With some plant materials, proteolytic digestion may be accompanied by the production of bitter-tasting digestion products. In such a situation, it may also be desirable to stop proteolytic digestion before maximum ACE inhibitory activity is reached to control the bitterness.

In one embodiment, the hydrolysates of the invention have an ACE inhibitory IC50 of less than 200 μg powder/ml. In further embodiments, the hydrolysates have an IC50 less than 100, or less than 60 or less than 50.

Typically, the proteolytic enzyme is used at a concentration from about 0.25% to about 8.0% w/w (enzyme:protein content).

In a further embodiment, the proteolytic enzyme is used at of concentration from about 0.5% to about 4.0%.

The proteolytic digestion is terminated by any suitable method, for example heat inactivation of the enzyme or adjustment of the pH of the digestion mixture away from the pH range of enzyme activity. Such methods are well known to those in the art. The resulting hydrolysate is filtered or centrifuged, for example in a decanter centrifuge, to remove residual meal or flour.

In accordance with a further embodiment of the invention is provided a process for preparing an ACE inhibitory peptide-containing hydrolysate from flax or canola meal by digesting the meal with a proteolytic enzyme to generate ACE inhibitory peptide-containing hydrolysates of high specific activity without further purification. Flax and canola have not previously been shown to be sources of ACE-inhibitory peptides. The proteolytic enzyme is selected, and the digestion carried out, as described above. The flax or canola meal may optionally be subjected to extraction with an organic solvent, as described above, before proteolytic digestion.

After digestion of a seed meal or flour to give ACE-inhibitory peptides, and separation of the hydrolysate from the residual meal or flour, the hydrolysate can be used as an edible product or may be spray dried to give a water-soluble powder suitable for use as an edible product or as a pharmaceutical. The use of protein and hydrolysed protein preparations as edible products and their incorporation into food products or use as food supplements is well known to those of skill in the food processing art, for example as described in Clemente, A (2000) "Enzymatic Hydrolysates in Human Nutrition", in Trends in Food Science & Technology v. 11, pp. 254-262

In one embodiment, the hydrolysates are used as edible products without further processing other than standard procedures to control bacterial contamination, such as flash pasteurisation or microfiltration.

The hydrolysates of the invention in liquid or powder form may be used to supplement beverages such as soft drinks, carbonated beverages, ready to mix beverages, milk and milk beverages and their derivates, and foods such as sauces, condiments, salad dressings, fruit juices, syrups, desserts (e.g, puddings, gelatin, icings, and fillings, baked goods and frozen desserts such as ice creams and sherbets), soft frozen products (e.g, soft frozen creams, soft frozen ice creams and yogurts, soft frozen toppings such as dairy or non dairy whipped toppings), oils and emulsified products (e.g., shortening, margarine, mayonnaise, butter and salad dressings), candy and bar confections, cereal foods, and chewing gum tablet.

It has long been realised that extremely raised blood pressure is a life threatening condition. It has more recently been suggested that even modest increases in blood pressure above normal may have deleterious effects.

A systolic blood pressure of 140 mm of mercury or greater, (occurring in approximately 20% of the adult population over the age of 30) is the current clinical definition of hypertension requiring medical intervention. A number of epidemiologists are, however, now defining a second or "preventative model" of hypertension which would define a systolic blood pressure of more than 120 mm of mercury as being the point at which people should undertake steps to reduce their blood pressure and associated risk of cardiovascular disease. People who have blood pressure within the range 120-140 mm mercury generally do not consider themselves to be sick and therefore are less likely to receive pharmaceutical based therapies. An increasing percentage of people in this category are, however, seeking non-pharmaceutical options to reduce this moderately elevated blood pressure (Potential benefits of functional foods and nutraceuticals to reduce the Risk and Costs of Diseases in Canada. B. J. Holub. Report to AAFC 2002).

The hydrolysates and powders of the invention provide anti-hypertensive agents which may be ideal for such cases of modestly raised blood pressure and can be consumed along with or as part of a food.

By comparison with the blood lowering effects previously observed in humans for ACE inhibitory products derived from milk or whey, the hydrolysates of the invention with IC50 values around 40-60 μg/ml may be given to human subjects at an initial dose from about 2 to about 5 gm per day. This dose may be adjusted as required once its blood pressure lowering effect is observed. The dosage would be adjusted accordingly for hydrolysates of higher or lower IC50 value, as would be understood by one of skill in the art.

The hydrolysates may also be formulated as tablets, capsules, granules, powders, syrups, suspensions or injectable solutions.

The hydrolysates produced by the methods described herein have equivalent or greater ACE inhibitory activity than the commercially available whey hydrolysates. When analysed by the ACE inhibitory assay described herein, the commercial whey product BioZate (Davisco Foods International) had an ACE inhibitory IC50 of 137 μg powder/ml. As shown herein, several plant materials yielded protein hydrolysates with ACE inhibitory IC50 values considerably less than that of the whey product, and therefore greater inhibitory activity, without the need to employ any subsequent purification strategy.

Hydrolysates obtained by proteolytic digestion of canola meal were further purified, as described in Example 12, to give two fractions, each containing a single purified ACE-inhibitory peptide. These peptides, not previously described as ACE inhibitors, have the amino acid sequences Val-Ser-Val and Phe-Leu.

The ACE inhibitory peptide-containing hydrolysates of the invention may be further processed to obtain fractions with further enhanced specific activity or the purified single peptides described above, for use as edible products or as pharmaceuticals.

The ACE inhibitory activity of the hydrolysates of the invention may be further enhanced, if desired, by ultrafiltration as described in the Examples herein.

It has been found that seeds with a high polysaccharide content, such as flax and barley, give hydrolysates of high viscosity. Where the viscosity of the hydrolysate is greater than about $10 \times 10^{-3}$ PaS (based on the viscosity of a 5% solution in water at 25° C. and a shear rate of 200 (l/s), ultrafiltration membranes up to pore size 100,000 MWCO can be used, but membranes with pore size up to 10000 are preferred.

For hydrolysates of lower viscosity, such as those obtained from canola, membranes of pore size up to 10000 MWCO may be used and membranes with pore size up to 3000 MWCO are preferred.

EXAMPLES

The examples are described for the purposes of illustration and are not intended to limit the scope of the invention.

Methods of chemistry, molecular biology, protein and peptide biochemistry and immunology referred to but not explicitly described in this disclosure and examples are reported in the scientific literature and are well known to those skilled in the art.

Reagents

Chemicals and enzymes were obtained as follows: angiotensin converting enzyme (from rabbit lung) and HHL (Sigma Chemical Co., St. Louis, Mo., USA); HA and trifluoroacetic acid (TFA) (Acros Organics, New Jersey, USA); HPLC grade acetonitrile (Fisher Scientific, Nepean, ON, Canada). All other chemicals were of reagent grade and also obtained from Fisher Scientific. HPLC-grade water was generated by a Milli-Q system (Millipore, Bedford, Mass., USA).

Methods

The Determination of ACE-Inhibitory Activity

The in vitro antihypertensive activity (ACE-inhibitory activity) was measured by a new improved HPLC method (Wu, J. P. et al., (2002)), modified from the method of Cushman and Cheung (1971). This method utilizes reverse phase high performance liquid chromatography (HPLC) to separate and quantify the ACE-catalyzed production of hippuric acid (HA). Hippuryl-histidyl-leucine (HHL) and HA were separated on a Symmetry $C_{18}$ column by gradient elution that used mixtures of trifluoroacetic acid (TFA)/acetonitrile and TFA/water as solvents. In comparison to the standard spectrophotometric method, the new HPLC method eliminates the need for ethyl acetate extraction of HA and allows direct injection of ACE reaction mixtures onto the HPLC column.

Sample Preparation for HPLC Analysis

For direct HPLC analysis, the total reaction volume was 70 μl, composed of 50 μl of 2.17 mM HHL, 10 μl of 2 mU of ACE and 10 μl of different concentrations of protein hydrolysates (all prepared with 100 mM borate buffer, containing 300 mM NaCl, pH 8.3). For the control test, 10 μl of buffer solution was used. The HHL and protein hydrolysates or the control buffer solutions, were combined and maintained at 37° C. for 10 min in 1.5 ml polyethylene micro-centrifuge tubes. ACE was also maintained at 37° C. for 10 min before the two solutions were combined and incubated at 37° C. in an Eppendorf Thermomixer R (Brinkmann Instruments, Inc. New York, USA) with continuous agitation at 450 rpm. The reaction was terminated after 30 min by addition of 85 μl of 1 N HCl and the solution filtered through a 0.45 μm nylon syringe filter for reverse phase RP-HPLC (RP-HPLC) analysis.

High-Performance Liquid Chromatography

HPLC was performed on a 2690 Separation Module equipped with a 996 Photodiode Array Detector (Waters Inc, MA. USA). Instrument control, data collection and analysis were undertaken using Millennium Chromatography Manager Software version 2.15 (Waters Inc, MA. USA). Samples (10 μl) were analyzed on a Symmetry C18 column (3.0×150 mm, 5 μm, Waters Inc., MA, USA) and HA and HHL were detected at 228 nm. The column was eluted (0.5 ml.min$^{-1}$) with a two solvent system: (A) 0.05% trifluoroacetic acid (TFA) in water and (B) 0.05% TFA in acetonitrile, with a 5-60% acetonitrile gradient for the first 10 min, maintained for two min at 60% acetonitrile, then returned to 5% acetonitrile for one min. This was followed by isocratic elution for four min at the constant flow rate of 0.5 ml.min$^{-1}$. External standard HA samples were prepared freshly and used for calculation of the concentration of HA formed by the action of ACE in the presence of protein hydrolysates ($HA_{hydrolysate}$) or in the absence of protein hydrolysate ($HA_{control}$), blank sample was prepared as: the ACE was inactivated first by the addition of HCl before the incubation.

ACE Inhibitory Activity Calculation

Inhibitory activity was calculated according to the following equation:

Inhibitory activity (%)=[($HA_{hydrolysate}$−$HA_{control}$)/($HA_{control}$−$HA_{blank}$)]×100

The IC50 value was defined as the amount of inhibitory substance in the reaction mixture that resulted in 50% inhibition of ACE activity, measured as described above. A plot of inhibition activity (%) versus concentration of protein hydrolysate (μg powder/ml) was generated using at least 5 different concentrations of the same hydrolysate sample. Regression was conducted with the Microsoft Excel 97 SR-1 software (Microsoft Corporation).

Determination of Degree of Hydrolysis (DH) of Proteins

Under alkaline or neutral conditions, the pH was monitored and maintained constant by addition of base. The amount of base added was recorded at set time intervals and used to calculate the degree of hydrolysis (DH). The DH is calculated from the volume and molarity of base to maintain constant pH and is expressed as the percent ratio of numbers of peptide bonds broken (h) to the total numbers of bonds per unit weight according to the formula of Adler-Nissen (1986).

Under acid hydrolysis conditions, the degree of hydrolysis (DH) was determined according to the method of Adler-Nissen J. (1979).

Hydrolysate Sample Preparation

Samples of hydrolysis reaction mixtures were drawn at various time intervals and quickly transferred to test tubes. From each sample, 2.0 ml aliquots were rapidly pipetted into each of two test tubes containing 10 ml of 1% $NaDodSO_4$, and the test tubes were kept at 75° C. by immersing in a water bath with shaking for at least 15 min to disperse the protein hydrolysate.

The contents of each test tube were transferred quantitatively to a 50-ml volumetric flask and diluted to volume with 1% $NaDodSO_4$. The content of free amino groups, expressed as leucine amino equivalents, was assayed by the TNBS reaction.

TNBS Reaction 0.25 ml prepared sample or blank (1.0% SDS) or standard solution was mixed with 2.0 ml of phosphate buffer at pH 8.2.

2 ml of 0.1% TNBS solution was added and the test tube was shaken and placed in 50° C. bath for 60 min, covered by aluminum foil.

4.00 ml of 0.1 N HCl was added to terminate the reaction and the absorbance was read against water at 340 nm after 30 min.

The DH was calculated using the modified method of Beak et al. (1995) as follows:

$$DH=(L_t-L_0)/(L_{max}-L_0)\times 100$$

where $L_t$ is the amount of α-amino acid released at time t; $L_0$ is the amount of α-amino acid in original canola solution; and $L_{max}$ is the maximum amount of α-amino acid in canola meal after acid hydrolysis (conducted under 6N HCl at 100° C. for 24 h).

Example 1

Enzymatic Screening for the Production of ACE Inhibitory Peptides (ACEIP) from Defatted Canola Meal The reaction was performed in batches in a reaction vessel equipped with a stirrer, thermometer, and pH electrode. Solvent extracted expeller cake commercial canola meal (Canbra Foods, Lethbridge, Alberta, Canada), (31.16 g), ground to pass a 40 mesh screen (protein content: 40.1%), was mixed thoroughly using a magnetic stirrer with distilled water to form 250 ml of a 5% protein slurry. The proteolytic enzymes evaluated are listed in Table 2, along with their optimum pH and temperature conditions. The pH of the slurry was adjusted to the appropriate pH and temperature for the enzyme being tested. Enzyme (4%, w/w on the basis of protein content of slurry) was added to initiate the reaction. The pH of the reaction was maintained at a constant value by addition of either 0.5 N NaOH or 1 N HCl. The volumes of alkali were recorded at specific intervals for the calculation of degree of hydrolysis (DH).

Samples were taken at 30, 60, 120, 180, 300 min intervals and enzyme was inactivated by heating in boiling water for 15 min. The pH of the slurry was then adjusted to pH 4.0 to precipitate unhydrolysed proteins, large peptides and all solids. The precipitate was removed by centrifugation at 10,000×g for 25 min. The resulting clear supernatants were then freeze dried and storied at −5° C. till further analysis. A control (without proteolytic enzyme) sample was also generated using the same procedure. The freeze dried supernatants were then evaluated for their ACE inhibitory activity.

The ACE inhibitory activity (%) of canola protein hydrolysates digested by different enzymes is shown in FIG. 1. Results indicated that ACE inhibitory activity (%) varied greatly, from 0% to 50.5%, with the average value of 28.4±13.47%. Alcalase 2.4 produced the most potent ACE inhibitory hydrolysate from canola meal. Other enzymes which generated significant ACE inhibitory activity included Protease S, Protease M, alkaline protease and neutral protease. Although not included in this study, Thermolysin was subsequently determined to produce a peptide fraction with similar ACE inhibitory activity to that observed for Alcalase 2.4 hydrolysates. Generally, any proteolytic enzyme which, in 3 hours digestion, generates a hydrolysate giving >35% ACE inhibition is preferred. No ACE inhibitory activity was detected for the unhydrolysed control canola meal samples, indicating that it was the breakdown of canola protein by the action of proteolytic enzymes that resulted in the formation of ACE inhibitory peptides. When the incubation time for Alcalase 2.4 and Protease M was extended to 24 hours there was no significant increase in the ACE inhibitory activity beyond 5 hours of incubation.

Figure 2:
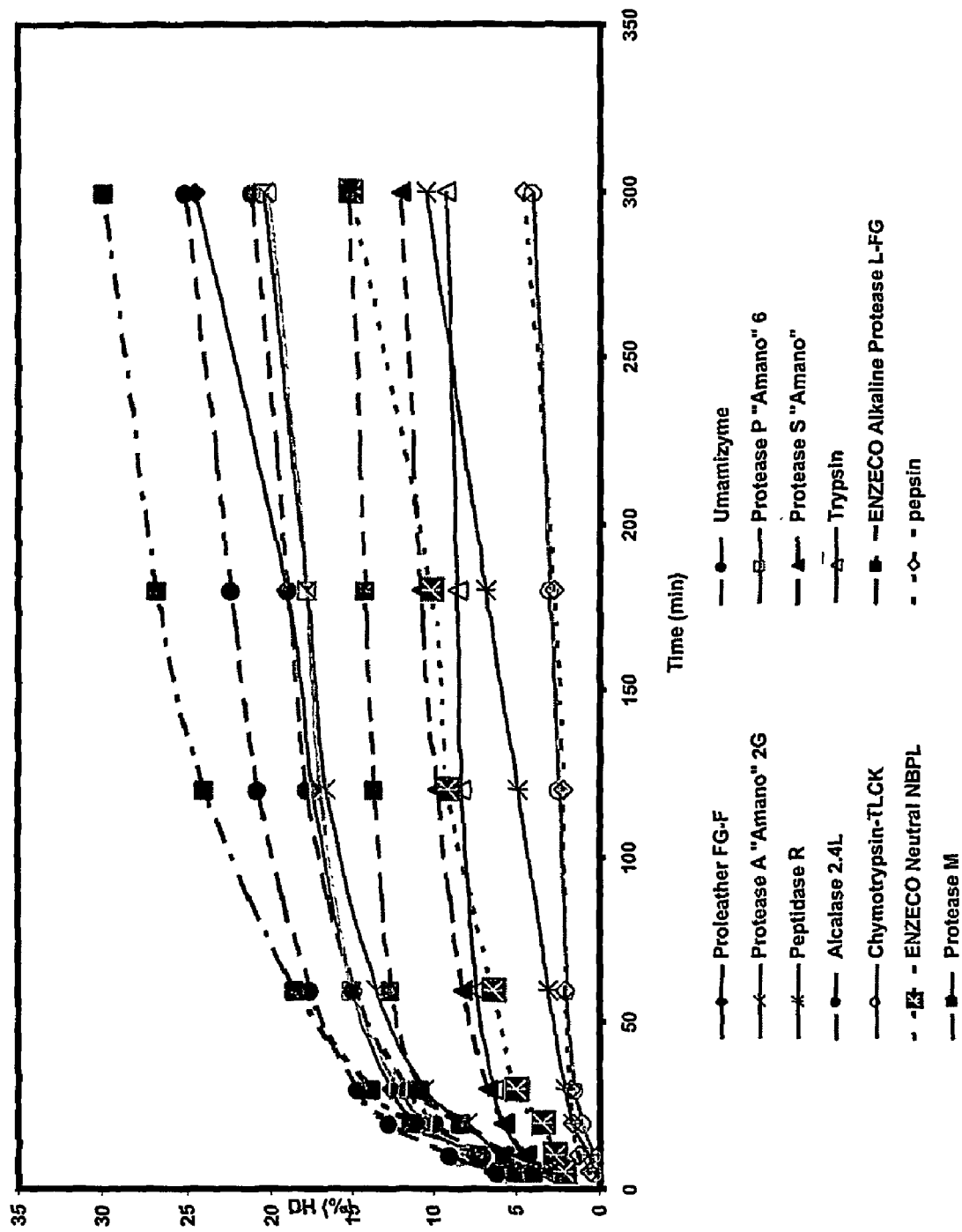
FIG. 2 shows degree of hydrolysis (DH-Y axis) as a function of incubation time (X axis), for various proteolytic enzymes acting on canola meal.

The relationship between degree of hydrolysis (DH) and incubation time is shown in FIG. 2; DH increased with increased incubation time. Alkaline Protease and Alcalase 2.4 gave the highest DH values. Protease M and Protease S enzyme treatments had moderate DH values, while their corresponding hydrolysates showed relatively high ACE inhibitory activity. Pepsin, Chymotrypsin and trypsin had the lowest DH values, which indicated that these enzymes had very limited ability to hydrolyse canola protein. There was no positive relationship between DH value and ACE inhibitory activity.

Sequential treatment of canola meal with different hydrolytic enzymes was investigated. After three hours of hydrolysis with Alcalase 2.4, the pH and temperature of the solution was adjusted to the optimum conditions for each of the four other enzymes that produced hydrolysates with high ACE inhibitory activity. The second enzyme was then added and the solution incubated for a further 3 hours. Of the protein hydrolystes resulting from sequential hydrolysis with two different enzymes, only the product derived from sequential hydrolysis with Alcalase 2.4 and Alkaline Protease had a significantly improved IC50 value (40.0 µg powder/ml) over the activity of the single enzyme product (Alcalase 2.4=68.6 µg powder/ml), or any of the other proteases by themselves (55.7-78.6 µg powder/ml).

Example 2

Preparation of Flaxseed Meal Enzymatic Hydrolysates

The reaction was performed in batches in a reaction vessel as in Example 1. Solvent extracted expeller cake commercial flaxseed meal (CanAmera Foods, Atton, Manitoba, Alberta) (50 g), ground to pass a 40 mesh screen (protein content: 33.9%), was mixed thoroughly using a magnetic stirrer with distilled water into a 750 ml slurry. The pH of the slurry was adjusted to 8.0 and temperature to 60° C. for Alcalase 2.4 enzyme hydrolysis. The enzyme was added at a ratio of 4% (w/w, on the basis of protein content of slurry). During the reaction, the pH of the slurry was maintained at a constant value by addition of 0.5 N NaOH. The enzyme was inactivated by adjusting the pH to around 4.0 with 6 N HCl. Unhydrolysed proteins, large peptides and insoluble material were removed by centrifugation at 6,000 g for 25 min. The residue was resuspended in 250 ml water and centrifuged under the same conditions. The resulting clear supernatants were then combined, freeze dried and stored at −5° C. till further analysis. At the same time, the control extract (without enzyme) was prepared under the same conditions. The hydrolysate yield was 53.54% (by weight) with a protein content of 39.9%, and an ACE inhibitory IC50 of 64.3 µg powder/ml.

A range of proteolytic enzymes was then evaluated, as in Example 1; results with flax were similar to those found with canola meal.

Example 3

Production of ACE Inhibitory Peptides from Soy Flour.

Nutrisoy 7B soy flour (87 g, Archer Daniels Midland CO., Decatur, Ill.) was mixed thoroughly using a magnetic stirrer with distilled water into 600 ml slurry. The slurry was adjusted to pH 8.0 and 60° C. for enzymatic hydrolysis by Acalase 2.4 as in Example 2. Enzyme was added at the ratio of 4% (w/w, on the basis of protein content of slurry). During the reaction, the pH of the slurry was maintained constant with 0.5 N NaOH. The enzyme was inactivated by adjusting the pH to around 4.0 with 6 N HCl. Unhydrolysed proteins and large peptides as well as other polymers were removed by centrifugation at 6,000×g for 25 min. The residue was resuspended in 300 ml water and centrifuged using the same conditions. The resulting clear supernatants were then combined and freeze dried and stored at −5° C. till further analysis. The hydrolysate produced by Alcalase 2.4 had an ACE inhibitory IC50 of 126.3 µg powder/ml with a product yield of 82.8% W/W.

Example 4

Production of ACE Inhibitory Peptides from Pea Flour and Oat Flour

Pea flour and oat flour (Parrheim Foods, Saskatoon, Canada) were incubated with Alcalase 2.4 under the same conditions as described in Example 2. The oat flour hydrolysate had the weakest ACE inhibitory activity (1200 µg powder/ml) of all the plant materials tested. Pea flour had an ACE inhibitory activity of IC50 87.1 µg powder/ml.

Example 5

Production of ACE Inhibitory Peptides from Whole Buckwheat Meal

Buckwheat was purchased from a local grocery store, ground and passed through a 40 mesh screen. Samples of the meal were hydrolysed with alcalase 2.4 L or Thermolysin, as described in Example 2. The protein hydrolysate produced by Thermolysin had an ACE inhibitory IC50 of 78.6 µg powder/ml with a product yield of 18%, while the ACE inhibitory IC50 of the Alcalase 2.4 L-treated hydrolysate was 174.3 µg powder/ml, with a product yield of 37.1%.

Example 6

Production of Ethanol-Treated Canola Meal ACE Inhibitory Hydrolysate

Defatted commercial canola meal as in Example 1 (31.2 g), ground to pass a 40 mesh screen, was extracted with 70% (v/v) ethanol:water solution at a ratio of 1:10 (weight/volume), with agitation for 12 hours at room temperature or at 50° C. for 3 hours. The meal was recovered, washed with distilled water and subjected to hydrolysis by Alcalase 2.4, Protease M, Protease S, or a sequential treatment of Alcalase 2.4 and Alkaline Protease, for a period not exceeding 3 hr per enzyme (combined incubation for total 6 hours). The ethanol-treated canola meal enzymatic digests were then fractionated by centrifugation to produce a supernatant containing the hydrolyzed peptides and a precipitate which contained the unhydrolyzed proteins and residual meal. These hydrolysates show ACE inhibitory activity (IC50) from 40.0 µg powder/ml to 64.3 µg powder/ml (Table 3). The protein content of the hydrolysates produced from ethanol-treated meal was significantly increased, from 41.7% to 54.6-60.4%, except for the hydrolysate resulting from incubation with Protease S where the protein content was only 28.7%.

Example 7

Preparation of Ethanol-Treated Defatted Flaxseed Meal Enzymatic Hydrolysates Defatted flaxseed meal as in Example 2 (50 g), ground to pass a 40 mesh screen (protein content: 33.9%), was treated with 70% (v/v) ethanol:water solution (1/15. w/v) at 50° C. for 3 hours. The extracted flaxseed meal was recovered by filtration and dispersed in water to form a 750 ml water slurry using a magnetic stirrer. The production of enzymatic hydrolysate with Alcalase 2.4 was performed as described as in Example 2. The ethanol-treated defatted flaxseed hydrolysate had a yield of 52.0% based on product weight, with a protein content of 45.5% and the ACE inhibitory IC50 was 51.4 µg powder/ml.

Defatted flaxseed meal recovered after the extraction of lignan (SDG) as reported by Westcott & Muir (U.S. Pat. No. 5,705,618), was also used for the production of ACE inhibitory hydrolysates. The protein hydrolysate generated by Alcalase 2.4 treatment of this material had a similar ACE inhibitory activity (IC50=55.7 µg powder/ml), indicating that the recovery of the valuable phytochemical SDG from the meal does not interfere with the ability to produce biologically active peptides from the residual meal.

Example 8

Production of ACE Inhibitory Peptides from Ethanol-Treated Soy Flour Using Alcalase 2.4 and/or Thermolysin Enzymes Nutrisoy 7B soy flour (87 g, Archer Daniels Midland CO., Decatur, Ill.) was treated with 70% ethanol for 3 hours at 50° C. The filtered residue was mixed thoroughly using a magnetic stirrer with distilled water into 600 ml slurry. The slurry was adjusted to the appropriate pH and temperature for digestion by Alcalase Acalase 2.4 L or Thermolysin, as in Table 2. The enzyme was added at a ratio of 4% (w/w, on the basis of protein content of slurry) for Alcalase 2.4 or at 1% (w/w, on the basis of protein content of slurry) for Thermolysin. During the reaction, the pH of the slurry was maintained constant with 0.5 N NaOH if necessary. The enzyme was inactivated by adjusting the pH to around 4.0 with 6 N HCl. Unhydrolysed proteins and large peptides as well as other polymers were removed by centrifugation at 6,000×g for 25 min. The residue was resuspended in 300 ml water and centrifuged using the same conditions. The resulting clear supernatants were then combined and freeze dried and storied at −5° C. till further analysis. The hydrolysate produced by Thermolysin had an ACE inhibitory IC50 of 42.9 µg powder/ml with a product yield of 64.7%, while Alcalase 2.4 treatment resulted in a hydrolysate with an ACE inhibitory IC50 of 118.1 µg powder/ml with a product yield of 55.7%.

Example 9

Production of ACE Inhibitory Peptides from Flaxseed Using Thermolysin

Defatted flaxseed meal as in Example 2 (50 g), ground to pass a 40 mesh screen (protein content: 33.9%) was mixed thoroughly using a magnetic stirrer with distilled water into a 750 ml slurry. The pH of the slurry was adjusted to the appropriate pH and temperature for the following enzymes: Thermolysin (39 units/mg solid), or incubation with Alcalase 2.4 for 3 hour and followed by incubation for a further 3 hours with Thermolysin. The enzyme was added at a ratio of 4% (w/w, on the basis of protein content of slurry) for Alcalase 2.4 or 1% (w/w, on the basis of protein content of slurry) for Thermolysin. After initiation of the reaction, the pH of the slurry was maintained at a constant value by addition of 0.5 N NaOH if necessary. The enzyme was inactivated by adjusting pH to around 4.0 with 6 N HCl. Unhydrolysed proteins and large peptides as well as other polymers were removed by centrifugation at 6,000×g for 25 min. The residue was suspended again with 250 ml water and centrifuged using the same conditions. The resulting clear supernatants were combined, freeze dried and stored at −5° C. till further analysis. The hydrolysate produced by Thermolysin had an ACE inhibitory IC50 of 37.1 µg powder/ml. The hydrolysate resulting from the sequential hydrolysis of Thermolysin and Alcalase 2.4 had an ACE inhibitory IC50 of 34.2 µg powder/ml. Thermolysin is a more effective enzyme for the production of ACE inhibitory peptides from flaxseed compared to Alcalase 2.4 alone which produced a hydrolysate with an IC50 of 64.3 mg powder/ml.

Example 10

Ultrafiltration Processing of Canola ACE Inhibitory Peptides

Defatted canola meal (62.3 g) ground to pass a 40 mesh screen was treated with 70% ethanol (v/v), at ratio of 1:10, W/V. After filtration to remove the aqueous alcohol, the residue was further digested by Alcalase 2.4 to produce an ethanol-treated canola protein hydrolysate. The resulting protein hydrolysate was further purified by ultrafiltration over 10000, 3000, 1000 molecular weight cut off (MWCO) membranes. Ultrafiltration was conducted using an Amicon Ultrafiltration Cell Model 8200 (Amicon Division, W.R. Grace & Co., Beverly, USA) by applying Argon at a pressure of 35 PSI to the solution on the retentate side of the membrane. The peptide hydrolyzate was initially separated into retentate and permeate fractions using a 10000 MWCO membrane. The permeate from the 10000 membrane was then subjected to ultrafiltration over the 3000 MWCO membrane to generate a 3000 MWCO retentate and a 3000 MWCO permeate. The 3000 MWCO permeate was further fractionated by ultrafiltration over a 1000 MWCO membrane to produce a 1000 MWCO permeate and a 1000 MWCO retentate. A second set of experiments were conducted where the total protein hydrolysate was subjected to ultrafiltration over the 3000 MWCO and 1000 MWCO membrane without prior treatment over the 10000 MWCO membrane. Permeates and retentates were collected and freeze dried for ACE inhibitory IC50 determination. All permeates contained peptides with greater ACE inhibitory activity than the corresponding retentate fractions. The highest ACE inhibitory activity (IC50=25.7 μg powder/ml) was found in the permeate obtained by direct ultrafiltration of protein hydrolysate over the 1000 MWCO membrane (Table 4). Peptide fractions with high ACE inhibitory activity (IC50=30.0-31.4 μg powder/ml) were also obtained by ultrafiltration over the 3000 MWCO membrane, either directly or after ultrafiltration over a 10000 MWCO membrane. Since the 3000 MWCO permeate product yield was higher that obtained with the 1000 MWCO membrane, there was little advantage in proceeding to the 1000 MWCO step. As membrane flux decreases with decreasing pore size, the optimum yield was obtained with the 3000 MWCO membrane.

Example 11

Ultrafiltration Processing of Flaxseed ACE Inhibitory Peptides

The liquid hydrolysates prepared in Examples 7 and 9 were further purified by ultrafiltration over 10000 and 100000 molecular weight cut off (MWCO) membranes as in Example 10. Ultrafiltration was conducted individually, both permeates and retentates were collected and freeze dried for ACE inhibitory IC50 determination. As in the previous example, all retentates contain peptides with greater ACE inhibitory activity than those found in the retentate (Table 5). The viscosity of the flaxseed hydrolyste was much greater than that observed for canola protein hydrolysates, therefore it was impracticable to conduct ultrafiltration with membranes of 3000 and 1000 MWCO. When operating with 10 K and 100 K MWCO membranes, difficulties were encountered when conducting ultrafiltration due to the formation of a film on the surface of the membrane. The formation of this film can be avoided by; A) stirring and heating the solution to a temperature greater than 40° C.; B) adjusting the pH to pH 3-4; or C) combination of A and B. Compared to the ACE inhibitory IC50 value of the original flaxseed hydrolysate (64.2 μg powder/ml), no significant improvement was achieved in these ultrafiltration steps since, because of the large pore size of the 100K MWCO membranes, large peptides can also pass through the membrane into the permeate. In the case of the ethanol-treated hydrolysate, the permeates had improved IC50 values of 30.0 and 35.7 μg powder/ml, compared to the original value at 51.4 μg powder/ml, indicating that the activity of the ACE inhibitory peptide fraction produced from the alcohol washed defatted flax meal can be improved by passage over either an 10K or a 100K MWCO membrane.

Example 12

Purification and Identification of Highly Bioactive ACE Inhibitory Peptides from Canola Protein Hydrolysates by Reversed Phase Chromatography Defatted canola meal Alcalase 2.4 hydrolysate prepared as in Example 6 was dissolved in 1% acetic acid water (v/v) solution at a concentration of 100 mg/ml for preparative chromatography. A segmented column composed of three Prep-Pak 40 mm Cartridges (Bondapack C-18 15-20 μm, 40×100 mm, Waters) and a guard column (40×10 mm) were coupled with a PrepLC 4000 system (Waters). Instrument control, data collection and analysis were undertaken using Millennium Chromatography Manager software v 2.15 (Waters Inc, MA. USA). The sample (20 ml) was injected automatically via solvent delivery system. The absorbance profile was monitored at 280 nm using a 2487 Absorbance Detector. Fractions were collected automatically using a Waters Fraction Collector. The column was eluted (50 ml.min$^{-1}$) with a two solvent system: A: water containing 1% acetic acid and B: methanol (100%) (Table 6).

All fractions collected were assessed for ACE inhibitory activity. A total of 32.6 g of canola meal Acalase hydrolysate was fractionated by preparative chromatography and the yield of the most active peptide fraction was 2.8 g (8.5%) with an ACE inhibitory IC50 of 2.0 μg powder/ml.

The active fraction from the preparative C-18 was further purified by Sephasil™ Peptide C18 ST 10/250 column (particle size: 12 μm, Pharmacia Biotech, Sweden) coupled with an ÄKTA explorer 10×T system controlled by Unicorn system (Pharmacia Biotech, Sweden). The column was eluted with a two solvent system: A: 20 mm sodium monobasic phosphate buffer solution (0.05% TFA) and B: 20 mm sodium monobasic phosphate (80% acetonitrile containing 0.05% TFA) at the flow rate of 5 ml/min, after 5 column volume (CV) iSocratic elution at 5% B, gradient elution from 5% B-20% B in 15 CV. The injection volume was 500 ml of a 200 mg/ml solution of the most active preparative chromatography fraction. The absorbance was monitored at 214 nm and fractions were collected. A total of 21 fractions were collected and the most potent fractions were $F_{13}$ and $F_{18}$. After repeat injection, 1.30 g of F13 and 0.85 g of F18 with ACE inhibitory (IC50 values of 38.6 and 312.9 μg powder/ml respectively) were obtained. These IC50's were higher than the starting material due to the presence of the non-volatile butters used in the chromatographic separation.

Each of $F_{13}$ and $F_{18}$ were re-chromatographed on a Sephasil™ Peptide $C_{18}$ ST 10/250 column (particle size: 12 um, Pharmacia Biotech, Sweden) using a two solvent system: A water (containing 0.1% TFA) and B acetonitrile (containing 0.1% TFA) at the gradient of 10% B −30% B in 7 CV at the flow rate of 5 ml/min to de-salt and further purify these active fractions. The major potent fraction peaks were identified as $F_{13-11}$ resulting from the chromatography of $F_{13}$, and $F_{18-5}$ from the chromatography of $F_{18}$. The yield for $F_{13-11}$ was 18.32 mg with an ACE inhibitory IC50 of 0.44 μg/ml, and for $F_{18-5}$ the yield was 4.89 mg with an IC50 value of 0.37 μg/ml.

Figure 3:
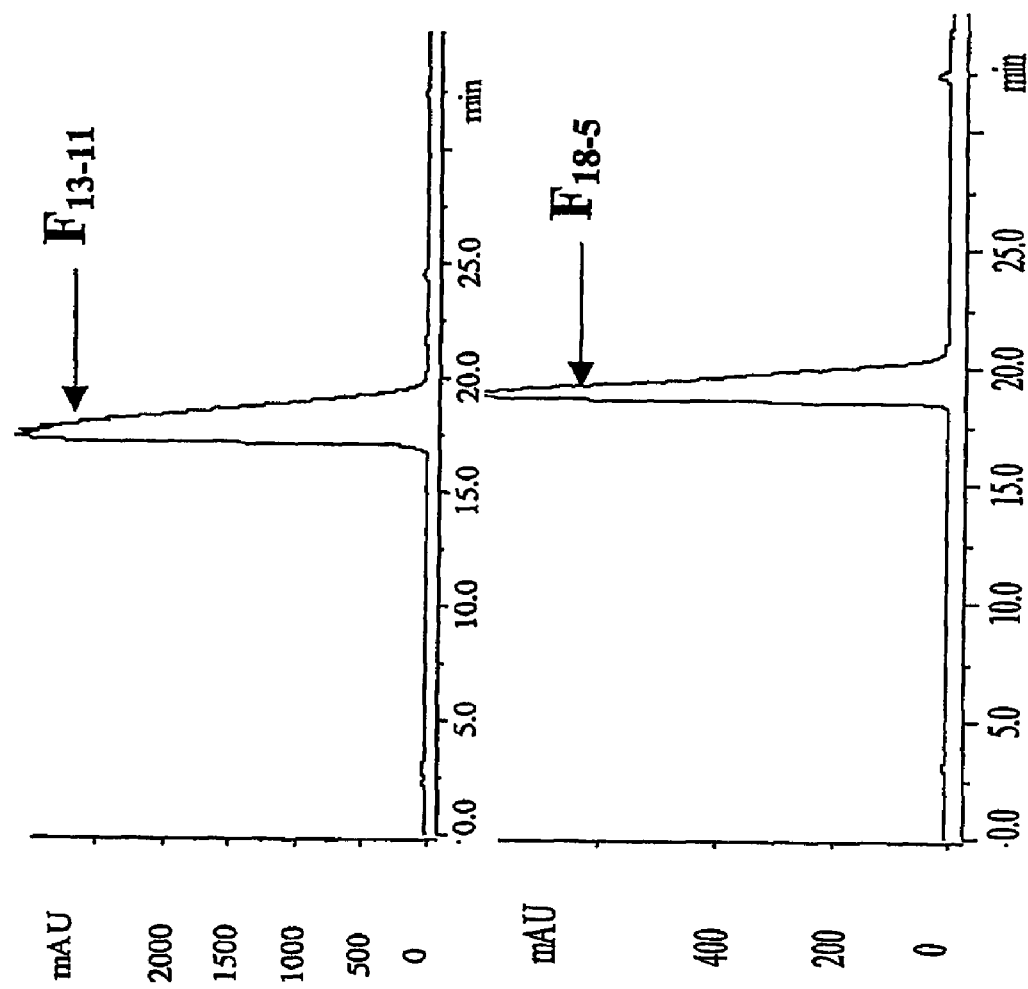
FIG. 3 shows absorbance at 214 nm (mAU) in fractions obtained from Sephasil Peptide $C_{18}$ 12µ ST4.6/250 column.

Fractions $F_{13-11}$ and $F_{18-5}$ were further purified (FIG. 3) by Sephasil Peptide C18 12 ST 4.6/250 column (Pharmacia Biotech, Sweden) using a two solvent system; A: water (containing 0.1% TFA) and B: acetonitrile (containing 0.1% TFA) with a gradient of 5% B −40% B in 10 CV at a flow rate of 1.5 ml/min. The injection volume was 30 ml of a 25 mg/ml solution. The absorbance was monitored at 214 nm and fractions were collected.

The identity of the peptides in the purified single peak fractions $F_{13-11a}$ and $F_{18-5a}$ from the ST 4.6/250 column were determined by atmospheric pressure chemical ionization (APCi) mass spectrometry using a Quattro LC liquid chromatograph/Mass Spectrometer (Micromass, UK) equipped with APCi probe, Z-Spray interface, separation module and photodiode array detector (Waters Inc. MA, USA). Instrument control and data analysis were performed using the MassLynx software (Micromass, UK). A peptide sample (10 ml) was chromatographed on a Symmetry $C_{18}$ column (2.0× 150 mm; 5 mm). The sample was eluted (0.3 ml.min$^{-1}$) with a two solvent system: (A) 0.1% formic acid (FA) in water and (B) 0.1% FA in acetonitrile, with a 5-60% acetonitrile gradient for the first 10 min, maintained for 2 min at 60% acetonitrile, then returned to 5% acetonitrile for 1 min. This was followed by isocratic elution for 4 min at the constant flow rate of 0.3 ml.min$^{-1}$. Positive and negative ion intensities were recorded from 50 to 500 m/z with a 1.5 sec scan time.

The analyzer vacuum was $2.2e^{-5}$ torr. The two most bioactive peptides were identified as Valine-Serine-Valine and Phenylanine-Leucine (Table 7).

Neither of these two amino acid sequences have previously been reported as having ACE inhibitory activity.

REFERENCES

Adler—Nissen, A., (1979), J. Agric. Food Chem., 27, 1256-1262;
Adler—Nissen, J. (1986), "Enzymic Hydrolysis of Food Proteins", Elsevier Applied Science Publishers, Barking, U.K.;
Beak et al., (1995), J. Food Sci., 60, 929-935;
Cushman et al., (1971), Biochem. Pharmacol., 20, 1637-1648;
Kawakami et al., (1975), in "Current Advances in Buckwheat Research", pp. 927-934;
Pedroche et al., (2002), J. Sci. Food Agric., 82, 960-965;
Skeggs et al., (1956), J. Exp. Med., 103, 259-299;
Westcott & Muir, U.S. Pat. No. 5,705,618;
Wu et al., (2002a), Food Res. Intnl., 35, 367-375;
Wu et al., (2002b), J. Chrom. A., 950(1/2), 125-130;
Yang et al., (1970), Biochem. Biophys. Acta, 214, 374-376;
Yano et al., (1996), Biosci. Biotechnol. Biochem., 60, 661-663.

TABLE 1

ACE inhibitory IC 50 for alcalase 2.4 digested plant hydrolysates

| Raw material | Ethanol extraction | IC50 (µg powder/ml) | Protein content (%) |
|---|---|---|---|
| canola meal | yes | 41.4 | 60.4 |
| canola meal | no | 68.6 | 41.7 |
| flax meal | yes | 51.4 | 45.5 |
| flax meal | no | 64.3 | 39.9 |
| pea flour | yes | 87.1 | 63.5 |
| pea flour | no | 131.4 | 59.3 |
| soy meal | yes | 126.3 | 63.8 |
| soy meal | no | 118.1 | 55.3 |
| oat flour | yes | 1198.6 | 8.3 |
| oat flour | no | 1044.3 | 14.2 |

TABLE 3

ACE inhibitory IC50 and protein content of ethanol-treated canola meal hydrolysates

| Enzyme | IC50 (µg powder/ml) | Protein (%) | Product Yield (%) |
|---|---|---|---|
| Protease S | 64.3 | 28.7 | 19.3 |
| Protease M | 40.0 | 56.4 | 32.8 |
| Alcalase 2.4 | 68.6 | 60.4 | 38.6 |
| Alcalase 2.4L + Alkaline Protease | 40.0 | 54.6 | 45.4 |

TABLE 4

ACE inhibitory IC50, protein content and yield of permeates and retentates resulting from the ultrafiltration treatment of canola hydrolysate

| | IC50 (µg powder/ml) | Protein content (%) | Product Yield (%) |
|---|---|---|---|
| stepwise operation | | | |
| 10,000 permeate | 37.1 | 59.3 | 73.5 |
| retentate | 54.3 | 54.0 | 20.4 |
| 3,000 permeate | 30.0 | 56.3 | 70.5 |
| retentate | 50.0 | 66.2 | 28.6 |
| 1,000 permeate | 30.0 | 46.9 | 43.5 |
| retentate | 31.4 | 68.5 | 47.0 |
| Individual operation | | | |
| 10,000 permeate | 37.1 | 59.3 | 73.5 |
| retentate | 54.3 | 54.0 | 20.4 |
| 3,000 permeate | 31.4 | 58.9 | 73.3 |
| retentate | 52.9 | 57.0 | 25.2 |
| 1,000 permeate | 25.7 | 50.3 | 56.0 |
| retentate | 52.9 | 68.0 | 35.7 |

TABLE 2

Hydrolysis of canola meal by various proteolytic enzymes

| Common Name | Trade Name | pH | T(° C.) | Source |
|---|---|---|---|---|
| Umamizyme | Umamizyme | 8 | 45 | Amano Pharmaceutical Co., Ltd. Japan |
| Protease A | Protease A "Amano" 2G | 7 | 50 | Amano Pharmaceutical Co., Ltd. Japan |
| Protease P | Protease P "Amano" 6 | 10 | 60 | Amano Pharmaceutical Co., Ltd. Japan |
| Peptidase R | Peptidase R | 7 | 45 | Amano Pharmaceutical Co., Ltd. Japan |
| Protease M | Protease M "Amano" | 4.5 | 50 | Amano Pharmaceutical Co., Ltd. Japan |
| Protease S | Protease S "Amano" | 8 | 70 | Amano Pharmaceutical Co., Ltd. Japan |
| Proleather FG-F | Proleather FG-F | 10 | 60 | Amano Pharmaceutical Co., Ltd. Japan |
| Alcalase 2.4 | Alcalase 2.4L | 8 | 60 | Novo Nordisk, North America, Inc., North Carolina. |
| Alkaline Protease | ENZECO Alkaline Protease L-FG | 10 | 50 | Enzyme Development Corporation, New York. |
| Neutral Protease | ENZECO Neutral Protease NBP-L | 7 | 40 | Enzyme Development Corporation, New York. |
| Pepsin | porcine stomach mucosa | 2 | 37 | Sigma, St. Louis, MO, USA. |
| Trypsin | Bovine Pancreas | 8 | 37 | Worthington Biochemical Corporation, NJ, USA. |
| Chymotrypsin | Bovine Pancreas | 8 | 25 | Worthington Biochemical Corporation, NJ, USA. |
| Thermolysin | Thermolysin | 8 | 55 | Sigma, St. Louis, MO, USA. |

TABLE 5

Yield, protein content and ACE inhibitory IC50 of defatted flax meal Alcalase 2.4 L hydrolysates subjected to ultrafiltration.

|  | IC50 (μg powder/ml) | Protein content (%) | Product Yield (%) |
|---|---|---|---|
| Defatted flaxseed hydrolysate |  |  |  |
| 100K permeate | 48.6 | 44.5 | 53.6 |
| 100K retentate | 54.3 | 32.1 | 39.3 |
| 10K permeate | 48.6 | 44.8 | 50.9 |
| 10K retentate | 61.4 | 31.6 | 39.0 |
| EtOH treated defatted flaxseed hydrolysate |  |  |  |
| 100K permeate | 30.0 | 52.3 | 45.6 |
| 100K retentate | 78.6 | 37.9 | 48.8 |
| 10K permeate | 35.7 | 53.5 | 54.8 |
| 10K retentate | 45.7 | 35.1 | 38.1 |

TABLE 6

PrepLC 4000 Gradient profile

| Time (min) | % A | % B | Flow rate (ml/min) |
|---|---|---|---|
| 0 | 100 | 0 | 50 |
| 10 | 100 | 0 | 50 |
| 188 | 55 | 45 | 50 |
| 198 | 100 | 0 | 50 |
| 208 | 100 | 0 | 50 |
| 211 | 100 | 0 | 0 |

TABLE 7

Identity of the two most potent ACE inhibitory peptides from the defatted canola alcalase 2.4 hydrolysate

|  | $F_{13-11}$ | $F_{18-5}$ |
|---|---|---|
| Sequence | Val-Ser-Val | Phe-Leu |
| Determined MW | 303.21 | 278.16 |
| Calculated MW | 303.18 | 278.16 |
| $IC_{50}$ (μg/ml) | 0.44 | 0.37 |

We claim:

1. A process for preparing an angiotensin converting enzyme (ACE) inhibitory peptide-containing hydrolysate comprising:
   a) contacting a substantially oil-free seed meal or a flour with an organic solvent selected from the group consisting of methanol, ethanol, propanol, butanol, acetone, ethyl acetate, and mixtures thereof;
   b) separating the meal or flour of step (a) from the solvent; and
   c) treating the separated meal or flour of step (b) with at least one proteolytic enzyme to produce an ACE inhibitory peptide-containing hydrolysate.

2. The process of claim 1 further comprising separating the treated seed meal or flour from the hydrolysate.

3. The process of claim 1 wherein the solvent is ethanol.

4. The process of claim 1 wherein the solvent is an aqueous organic solvent.

5. The process of claim 4 wherein the solvent is 70:30 v/v ethanol:water.

6. The process of claim 1 wherein the seed meal or flour is contacted with the solvent at a temperature from about 20° C. to the boiling point of the solvent for a period of time from about one hour to about 24 hours.

7. The process of claim 1 wherein the ACE inhibitory peptide-containing hydrolysate is ultrafiltered.

8. The process of claim 7 wherein the hydrolysate is ultrafiltered using an ultrafiltration membrane of pore size from about 1000 to about 100,000 molecular weight cut-off (MWCO).

9. The process of claim 1 wherein the hydrolysate is dried to form a powder.

10. The process of claim 1 wherein the seed meal or flour is from a plant selected from the group consisting of flax, canola, soybean, cottonseed, sunflower, peanut, mustard, pea, lentil, bean, chickpea, wheat, oats, barley, rye and buckwheat.

11. The process of claim 1 wherein the at least one proteolytic enzyme is present at a concentration from about 0.25% to about 8.0% w/w (enzyme:protein content).

12. The process of claim 1 wherein the at least one proteolytic enzyme is present at a concentration from about 0.5% to about 4.0% w/w (enzyme:protein content).

13. The process of claim 1 wherein the at least one proteolytic enzyme is selected from the group consisting of a protease, a peptidase, a serine endopeptidase and a metalloendopeptidase.

14. The process of claim 1 wherein the at least one proteolytic enzyme is an alkaline protease and the reaction mixture is adjusted to an alkaline pH by addition of a base selected from the group consisting of NaOH, KOH and $NH_4OH$.

15. The process of claim 14 wherein the added base is KOH.

16. The process of claim 1 wherein the at least one proteolytic enzyme is an acid protease and the reaction mixture is adjusted to an acidic pH.

17. The process of claim 1 wherein the degree of proteolysis is controlled by varying the incubation time.

18. The process of claim 1 wherein the seed meal is canola meal and the hydrolysate contains the peptide Val-Ser-Val.

19. The process of claim 1 wherein the seed meal is flax meal or soybean meal and the proteolytic enzyme is a metalloendopeptidase.

20. A process for preparing an angiotensin converting enzyme (ACE) inhibitory peptide-containing hydrolysate from a plant selected from the group consisting of flax, canola, soybean, cottonseed, sunflower, peanut, mustard, pea, lentil, bean, chickpea, wheat, oats, barley, rye and buckwheat, the process comprising:
   a) contacting a substantially oil-free seed meal or a flour with an organic solvent selected from the group consisting of methanol, ethanol, propanol, butanol, acetone, ethyl acetate, and mixtures thereof;
   b) separating the meal or flour of step (a) from the solvent; and
   c) treating the separated meal or flour of step (b) with at least one proteolytic enzyme to produce an ACE inhibitory peptide-containing hydrolysate.

* * * * *